United States Patent [19]

Heeres et al.

[11] Patent Number: 4,483,865

[45] Date of Patent: Nov. 20, 1984

[54] ANTIMICROBIAL IMIDAZOLE DERIVATIVES

[75] Inventors: Jan Heeres, Vosselaar; Leo J. J. Backx, Arendonk; Joseph H. Mostmans, Antwerp, all of Belgium

[73] Assignee: Janssen Pharmaceutica N.V., Beerse, Belgium

[21] Appl. No.: 342,553

[22] Filed: Jan. 25, 1982

Related U.S. Application Data

[63] Continuation-in-part of Ser. No. 248,594, Mar. 27, 1981, abandoned.

[51] Int. Cl.$^3$ .................. A01N 43/50; C07D 403/00; C07D 233/54
[52] U.S. Cl. ............................... 424/273 R; 548/336; 548/341
[58] Field of Search ..................... 548/336; 424/273 R

[56] References Cited

U.S. PATENT DOCUMENTS

| | | | |
|---|---|---|---|
| 3,193,563 | 7/1965 | Cross | 260/397 |
| 3,575,999 | 4/1971 | Godefroi et al. | 548/336 |
| 4,055,652 | 10/1977 | Walker | 424/273 R |
| 4,078,071 | 3/1978 | Walker | 424/273 R |
| 4,079,062 | 3/1978 | Reet et al. | 260/340.7 |
| 4,101,666 | 7/1978 | Heeres | 424/273 R |
| 4,150,153 | 4/1979 | Walker | 548/336 |
| 4,359,475 | 11/1982 | Walker | 424/273 R |

*Primary Examiner*—Ethel G. Love
*Attorney, Agent, or Firm*—Geoffrey G. Dellenbaugh

[57] ABSTRACT

The invention is concerned with novel dithioketal derivatives of 1-(2-aryl-2-oxoethyl)-1H-imidazoles and sulfones and sulfoxides derived therefrom, said compounds being useful as antimicrobial agents.

23 Claims, No Drawings

ANTIMICROBIAL IMIDAZOLE DERIVATIVES

CROSS-REFERENCE TO RELATED APPLICATION

This is a continuation-in-part of our copending application Ser. No. 248,594, filed Mar. 27, 1981, now abandoned.

BACKGROUND OF THE INVENTION

Ketal derivatives of 1-(2-aryl-2-oxoethyl)-1H-imidazoles are disclosed, inter alia, in the following references:

U.S. Pat. No. 3,575,999; and
U.S. Pat. No. 4,079,062.

D.O.S. No. 2,604,487, in the broadest meaning of its scope, theoretically embraces dithioketals of 1-(2-aryl-2-oxoethyl)-1H-imidazoles or possible starting materials for the preparation of metal salt complexes with antifungal activity. Nowhere in said reference is there any description or any other indication of particular dithioketals.

The compounds of the present invention are nowhere disclosed in the prior art and are deemed to be novel.

DESCRIPTION OF THE PREFERRED EMBODIMENTS

The subject invention relates to a series of novel dithioketal derivatives of 1-(2-oxo-2-phenylethyl)-1H-imidazoles and the corresponding sulfones and sulfoxides thereof, being represented by the formula

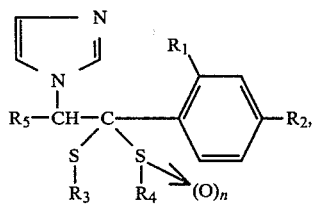

the possible stereochemically isomeric forms the acid addition salts and the metal salt complexes thereof, wherein:

$R_1$ and $R_2$ are each independently selected from the group consisting of hydrogen, halo and methyl;

$R_3$ and $R_4$ are each independently selected from the group consisting of $C_1$–$C_6$-lower alkyl and $C_3$–$C_4$-lower alkenyl, or $R_3$ and $R_4$ form, together with the sulfur atoms to which they are attached and the bridging carbon atom, a 5, 6 or 7-membered ring which is optionally substituted with 1 to 4 $C_1$–$C_4$-lower alkyl groups;

$R^5$ is a member selected from the group consisting of hydrogen, $C_1$–$C_4$-lower alkyl, 2-propenyl and 2-propynyl; and n is 0, 1 or 2.

As used in the foregoing and in the following definitions, "halo" is generic to fluoro, chloro, bromo and iodo; "lower alkyl" is meant to include straight and branched hydrocarbon radicals having a number of carbon atoms within the indicated limits, such as, for example, methyl, ethyl, propyl, 1-methylethyl, butyl, 1-methylpropyl, 2-methylpropyl and 1,1-dimethylethyl for $C_1$–$C_4$- lower alkyl and, for $C_1$–$C_6$-lower alkyl the foregoing plus the different isomers of pentyl and hexyl.

Preferred compounds within the scope of formula (I) are those wherein $R_1$ is hydrogen or chloro and $R_2$ is chloro.

Particularly preferred are compounds of formula (I) wherein $R_1$ is hydrogen or chloro, $R_2$ is chloro and $R_3$ and $R_4$ together with the sulfur atoms to which they are attached and the bridging carbon atom form a 5 or 6-membered ring which is optionally substituted with a $C_1$–$C_3$-lower alkyl radical.

Especially preferred are compounds of formula (I) wherein $R_1$ is hydrogen or chloro, $R_2$ is chloro, $R_3$ and $R_4$ together with the sulfur atoms to which they are attached and the bridging carbon atom form a 5- or 6-membered ring which is optionally substituted with a $C_1$–$C_3$-lower alkyl radical and $R_5$ is hydrogen or $C_1$–$C_4$-lower alkyl.

More especially preferred are compounds of formula (I) wherein $R_1$ is hydrogen or chloro, $R_2$ is chloro, $R_3$ and $R_4$ together with the sulfur atoms to which they are attached and the bridging carbon atom form a 5- or 6-membered ring which is optionally substituted with a $C_1$–$C_3$ lower alkyl radical and $R_5$ is hydrogen.

Most especially preferred are compounds of formula (I) wherein $R_1$ and $R_2$ are both chloro, $R_3$ and $R_4$ together with the sulfur atoms to which they are attached and the bridging carbon atom form a 5-membered ring which is optionally substituted with a methyl, ethyl or propyl group and $R_5$ is hydrogen.

Preferred species within the scope of formula (I) are the following:

1-[[2-(2,4-dichlorophenyl)-1,3-dithiolan-2-yl]methyl]-1H-imidazole;

1-[[2-(2,4-dichlorophenyl)-4-methyl-1,3-dithiolan-2-yl]methyl]-1H-imidazole;

1-[[2-(2,4-dichlorophenyl)-4-ethyl-1,3-dithiolan-2-yl]methyl]-1H-imidazole;

1-[[2-(2,4-dichlorophenyl)-4-propyl-1,3-dithiolan-2-yl]methyl]-1H-imidazole; and 2-(2,4-dichlorophenyl)-2-[1-(1H-imidazol-1-yl)ethyl]-1,3-dithiolane.

The compounds of formula (I) wherein n is 0, said compounds being represented by the formula (I-a)

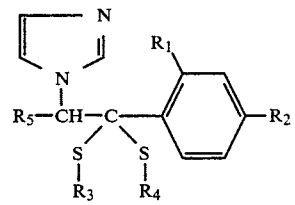

may be prepared by subjecting an appropriate ketone of the formula (II)

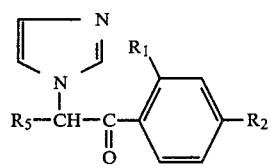

or an appropriate ketal derivative thereof to a thioketalization reaction with an appropriate thiol of the formula

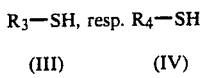

or a dithiol of the formula

wherein $R_3$ and $R_4$ are as defined in formula (I).

The said thioketalization reaction is advantageously carried out in the presence of an appropriate Lewis acid, and, unless the acid itself has suitable solvent properties, preferably in an appropriate reaction-inert organic solvent.

Suitable Lewis acids which may be used in the above procedure include strong protonic acids, e.g. sulfonic acids such as methanesulfonic, benzenesulfonic and 4-methylbenzenesulfonic acid, and non-protonic Lewis acids such as, for example, aluminum chloride, zinc chloride, tin chloride and the like.

Appropriate solvents include, for example, aliphatic and aromatic hydrocarbons, e.g. hexane, cyclohexane, heptane, benzene, methylbenzene, dimethylbenzene and the like; chlorinated hydrocarbons such as, for example, di-, tri- and tetrachloromethane, 1,2-dichloroethane, 1,1,2,2-tetrachloroethane, tetrachloroethene and the like; and ethers such as tetrahydrofuran and 1,4-dioxane. In order to enhance the reaction rate, particularly when a protonic acid is used, there may be added to the reaction mixture an appropriate tri(lower alkyloxy)methane, preferably 1,1′,1″-[methylidynetris(oxy)]tris(ethane). Elevated temperatures are advantageous and, preferably, the reaction is carried out at the reflux temperature of the reaction mixture. Ketal derivatives of the ketones (II) which may be used as starting materials include di-lower alkylketals, such as the dimethyl-, diethyl-, dipropyl- and dibutyl ketals and cyclic ketals such as the dioxolane ketals derived from ethanediol.

The compounds of formula (I) wherein n is 1 or 2, said compounds being represented by the formula (I-b), respectively (I-c), can be derived from the corresponding (I-a) by oxidizing the latter with an appropriate oxidizing agent. By appropriately selecting the oxidizing agent and the reaction circumstances either sulfones or sulfoxides can be obtained substantially free from the other.

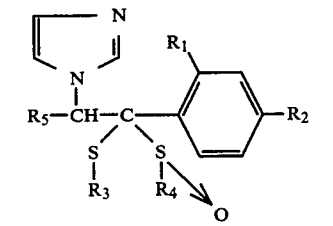 (I-b)

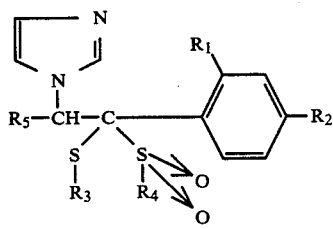 (I-c)

Appropriate oxidizing agents include, for example, periodates, e.g., sodium periodate, potassium periodate and the like; peroxides, e.g., hydrogen peroxide and the like; and peracids, e.g. perbenzoic acid and preferably 3-chloroperbenzoic acid. These oxidation reactions may be carried out by methodologies which are well-known in the art.

The ketones of formula (II) and the corresponding ketals which are used as starting materials are well-known. Such compounds are described for example in:
Brit. Pat. No. 2,026,486;
Brit. Pat. No. 2,027,701; and
Brit. Pat. No. 1,533,706.

The thiols of formulas (III), (IV) and (V) are generally known and may all be prepared by the application of art-known methodologies.

It is obvious from formula (I) that the compounds of the present invention may possibly exist under different stereochemically isomeric forms.

Whenever n is the integer 1 or 2 and/or $R_3$ and $R_4$ are not identical or form an alkylene radical which is unsymmetrically substituted, the carbon atom bearing the two sulfur atoms is an asymmetrically substituted carbon atom. Additional chiral centers may exist in $R_3$ and $R_4$ and when $R_5$ is other than hydrogen. Each of these chiral centers may exist in a R- and S-configuration, this R- and S-notation being in correspondance with the rules described by R. S. Cahn, C. Ingold and V. Prelog in Angew. Chem., Int. Ed. Engl., 5, 385–511 (1966).

Pure stereochemically isomeric forms of the compounds of formula (I) may be obtained by the application of art-known procedures. Diastereoisomers may be separated by physical separation methods such as selective crystallization and chromatography techniques, e.g., counter current distribution, and enantiomers may be separated from each other by the selective crystallization of their diastereoisomeric salts with optically active acids.

Pure stereochemically isomeric forms may also be derived from the corresponding pure stereochemically isomeric forms of the appropriate starting materials, provided that the reaction occurs stereospecifically. Stereochemically isomeric forms of the compounds of formula (I) are naturally intended to be embraced within the scope of the invention.

In view of their basic properties, the compounds of formula (I) may be converted into their acid addition salt forms by reacting them with appropriate acids such as, for example, inorganic acids, e.g., hydrochloric, hydrobromic, hydroiodic, sulfuric, phosphoric, phosphonic, nitric and the like acids, or organic acid, e.g., acetic, propanoic, hydroxyacetic, 2-hydroxypropanoic, 2-oxopropanoic, ethanedioic, propanedioic, butanedioic (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, hydroxyethanesulfonic, 4-methylbenzenesulfonic, 2-hydroxybenzoic, 4-amino-2-hydroxybenzoic, 2-phenoxybenzoic, 2-acetyloxybenzoic, 2,4-hexadienoic or 1,5-naphthalenedicarboxylic acid.

Metal salt complexes of formula (I) may be obtained by the complexation-reaction of an imidazole of formula (I) with an organic or inorganic metal salt such as, for example, hydrohalides, nitrates, sulfates, phosphates, 2,3-dihydroxybutanedioates and the like of copper, manganese, zinc, iron and the like transition metals, which may be present in each of their possible valencies.

Stoechiometrically defined metal salt complexes may be prepared by dissolving a compound of formula (I) in a water-miscible solvent (e.g. warm ethanol, methanol, 1,4-dioxane or N,N-dimethylformamide) and adding thereto an aqueous solution of the desired metal salts such as, for example, $CuSO_4.5H_2O$, $Mn(NO_3)_2.4H_2O$, $FeCl_3.6H_2O$ and the like.

The foregoing enumerations are intended to illustrate and not to limit the scope of the present invention.

The compounds of formula (I) and the acid addition salts and metal salt complexes have potent antimicrobial, in particular antifungal, properties and as such they can be used for combating the growth of microorganisms in and/or on living and non-living materials of any nature.

Particularly, the compounds of formula (I) possess a very advantageous antimicrobial spectrum, rendering them useful for the protection of crops without causing undesired side-reactions. Examples of crops within the scope of this invention are the followings: cereals, maize, rice, vegetables, sugar-beet, soybeans, groundnuts, fruit-trees, ornamentals, grapevines, hops, cucurbitaceae (gherkins, cucumbers, melons), solanaceae such as potatoes, tobacco and tomatoes, as well as bananas, cocoa and rubber.

The compounds of formula (I) can be used to reduce or destroy fungal growth on plants of these or related crops or on parts of such plants (e.g., fruits, blossoms, foliage, stams, tubers, roots), whereby the newly outgrowing parts of such plants are also protected against fungal attack. The compounds of this invention are active against phytophathogenic fungi belonging to the following classes: Ascomycetes (e.g. Erysiphaceae, Fusarium, Helminthosporium); Basidiomycetes such as particularly rust-fungi (e.g, Puccinia); Fungi imperfecti (e.g., Moniliales etc., Cercospora and Botrytis) and Oomycetes belonging to the class of the Phycomycetes such as, for example, Phytophthora and Plasmopara. They can further be used as seed-dressings for the treatment of seed (e.g. fruits, tubers, grains) and cuttings to protect them from fungal infection, and against fungi occuring in the soil.

The compounds of formula (I) can be used alone or in admixture with appropriate carriers and/or additives. Appropriate carriers and additives can be solid or fluid and are generally known in the art of formulating, such as, for example, natural and regenerated mineral substances, solvents, dispersants, wetting agents, adhesives, thickeners, binders or fertilizers.

The concentration of the active ingredient in commercial preparations can vary from about 0.1 to about 90%.

For their application the compounds of formula (I) can be formulated in the following composition-forms (whereby suitable concentrations of the active ingredient are indicated within brackets):
solid compositions: dusts (up to 10%), granulates, coated granulates, impregnated granulates and homogeneous granulates, pellets (from 1 to 80%);
liquid compositions:
 (a) water-dispersible concentrates: wettable powders and pastes (25-90% in commercial form, 0.01-15% in the ready for use solution); emulsion-and solution-concentrates (10-50%; 0.01-15% in ready for use solution);
 (b) solutions (0.1-20%); aerosols.

If desired, in order to extend their spectrum of activity the compounds of formula (I) may be combined with other appropriate pesticides such as, for example, fungicides, bactericides, insecticides, acaricides, herbicides, plant-growth regulators and the like. Such compositions are intended to be within the scope of the present invention.

The content of active substance in the above agents is from 0.1 to 95%, preferably from 1 to 80%. The forms may be diluted from this concentration down to 0.001%. The employed doses are in general from 0.01 to 10 kg of active substance pro ha, preferably from 0.025 to 5 kg/ha.

Due to their broad antifungal spectrum the compounds of formula (I) are especially useful as seed-dressings, in the preservation of human and animal feeding stuffs, in particular animal fodder, and, generally, in the protection of non-living materials such as, for example, coatings, e.g., oil paints, dispersion paints, lacquers, whitewash; wood, e.g., timber, lumber, railway sleepers, telephonepoles, fences, wood coverings, wickerwork, plywood, particle board, clipboard, joinery, bridges or wood products which are generally used in housebuilding, or pulp wood used in paper manufacture; textiles, e.g., carpets, canvas, awnings, fishing nets, ropes and packing materials; and other materials of diverse nature such as, for example joint fillings of tile walls, tiles in polymeric materials, paper-hangings, hides, leather, artificial leather, bath carpets, shower curtains, technical devices in plastic, glues, mortar as well as walls which are penetrated or fouled by organic materials, cutting oils, fuel oils and the like.

The materials which are treated with agents according to the invention are protected from moulding, rotting, loss of their useful mechanical properties such as breaking strength, resistance to shock and shearing strength; or decay of their optical or other useful properties such as the occurence of odor, staining, spot formation and dote caused by the following microorganisms: Aspergillus species, Penicillium species, Verticillium species, Alternaria species, Rhizopus species, Mucor species, Paecelomyces species, Saccharomyces species, *Trichoderma viride, Chaetomium globosum, Stachybotrys atra, Myrothecium verrucaria, Oospora lactis* and other woodrot and wood decay fungi.

Special emphasis should be led on the good activity against moulds such as *Aspergillus niger, Penicillium funiculosum, Trichoderma viride, Alternaria alternata,* fungi such as *Chaetomium globosum, Trychophyton mentagrophytes, Coriolus versicolor, Coniophora cerebella, Poria monticola, Merulius (Serpula) lacrymans* and *Lenzites trabea,* and yeasts such as *Candida albicans* and Saccharomyces species.

The compounds of formula (I) may be used in agents according to the present invention on their own or in combination with appropriate carriers and/or other additives. Appropriate carriers and additives can be solid or liquid and correspond to the substances usually used in formulation techniques such as natural or regenerated inorganic substances, solvents, dispersants, emulsifiers, wetting agents, adhesion agents, thickeners or binding agents.

The compounds of formula (I) show good solubility in organic solvents and in driving gases for aerosols. The lack of color and odor of the compounds of formula (I) is in this connection of great practical value.

The following examples are intended to illustrate and not to limit the scope of the present invention. Unless otherwise indicated all parts therein are by weight.

A. EXAMPLES OF CHEMICAL PREPARATION

EXAMPLE I

A mixture of 1 part of 4-methylbenzenesulfonic acid and 90 parts of dimethylbenzene was distilled azeotropically to dry. Then there were added 5 parts of 1-[2-(2,4-dichlorophenyl)-2,2-dimethoxyethyl]-1H-imidazole 4-methylbenzenesulfonate, 4.7 parts of 1,2-ethanedithiol and 1.5 parts of 1,1',1''-[methylidynetris(oxy)]trisethane and the whole was stirred and refluxed for 8 days with water-separator. The reaction mixture was cooled and stirred with a sodium hydroxide solution 20%. The whole was poured onto water and the product was extracted with 2,2'-oxybispropane. The extract was washed with water, dried, filtered and evaporated. The residue was purified by column-chromatography over silica gel using a mixture of trichloromethane and methanol (98:2 by volume) as eluent. The pure fractions were collected and the eluent was evaporated. The residue was converted into the nitrate salt in 4-methyl-2-pentanone and 2,2'-oxybispropane. The salt was filtered off and crystallized from 2-propanol, yielding 1.7 parts (43%) of 1-[[2-(2,4-dichlorophenyl)-1,3-dithiolan-2-yl]methyl]-1H-imidazole nitrate; mp. 184.7° C.

The compounds prepared according to Example I or prepared in an analogous manner are listed in the following table I.

TABLE I

Compounds of formula I

| No. | $R_1$ | $R_2$ | $R_3,R_4$ | n | Salt form | phys. data |
|---|---|---|---|---|---|---|
| 1 | Cl | Cl | —CH$_2$—CH$_2$— | 0 | HNO$_3$ | mp. 184.7° C. |
| 2 | Cl | Cl | —CH$_2$—CH$_2$— | 0 | HCl | mp. 236.7° C. |
| 3 | H | Cl | —CH$_2$—CH$_2$— | 0 | — | — |
| 4 | CH$_3$ | Br | —CH$_2$—CH$_2$— | 0 | — | — |
| 5 | H | CH$_3$ | —CH$_2$—CH$_2$— | 0 | — | — |
| 6 | Br | Br | —CH$_2$—CH$_2$— | 0 | — | — |
| 7 | Cl | Cl | —CH$_2$—CH(CH$_3$)— | 0 | HNO$_3$ | mp. 167.0° C. |
| 8 | Cl | Cl | —CH$_2$—CH(C$_2$H$_5$)— | 0 | cis + trans.HCl | mp. 220.0° C. |
| 9 | Cl | Cl | —CH$_2$—CH(C$_3$H$_7$)— | 0 | cis + trans.HCl | mp. 204.8° C. |
| 10 | Cl | Cl | —CH$_2$—CH(C$_4$H$_9$)— | 0 | — | — |
| 11 | Cl | Cl | —CH(CH$_3$)—CH(CH$_3$)— | 0 | — | — |
| 12 | Cl | Cl | —CH(CH$_3$)—CH(C$_2$H$_5$)— | 0 | — | — |
| 13 | Cl | Cl | —CH$_2$—CH$_2$—CH$_2$— | 0 | — | — |
| 14 | Cl | Cl | —CH$_2$—CH$_2$—CH(CH$_3$)— | 0 | — | — |
| 15 | Cl | Cl | —CH(CH$_3$)—CH$_2$—CH(CH$_3$)— | 0 | — | — |
| 16 | Cl | Cl | —CH$_2$—C(CH$_3$)$_2$—CH$_2$— | 0 | — | — |
| 17 | Cl | Cl | —(CH$_2$)$_4$— | 0 | — | — |
| 18 | Cl | Cl | —CH$_3$, —CH$_3$ | 0 | — | — |
| 19 | Cl | Cl | —C$_2$H$_5$, —C$_2$H$_5$ | 0 | — | — |
| 20 | Cl | Cl | —C$_3$H$_7$, —C$_3$H$_7$ | 0 | — | — |
| 21 | Cl | Cl | —C$_4$H$_9$, —C$_4$H$_9$ | 0 | — | — |
| 22 | Cl | Cl | —CH$_2$—CH=CH$_2$, —CH$_2$—CH=CH$_2$ | 0 | — | — |
| 23 | Cl | Cl | —CH$_2$—CH$_2$— | 1 | — | — |
| 24 | Cl | Cl | —CH$_2$—CH$_2$— | 2 | — | — |
| 25 | Cl | Cl | —CH$_2$—CH(CH$_3$)— | 1 | — | — |
| 26 | Cl | Cl | —CH$_2$—CH(C$_2$H$_5$)— | 1 | — | — |
| 27 | Cl | Cl | —CH$_2$—CH(C$_3$H$_7$)— | 1 | — | — |
| 28 | Cl | Cl | —(CH$_2$)$_3$ | 1 | — | — |

EXAMPLE II

A mixture of 6 parts of 1-(2,4-dichlorophenyl)-2-(1H-imidazole-1-yl)-1-propanone and 30 parts of methanesulfonic acid was stirred till all solid entered solution. After cooling, 5.5 parts of 1,2-ethanedithiol were added while nitrogen gas was introduced. The whole was stirred overnight at room temperature. The reaction mixture was diluted with trichloromethane till a volume of 150 parts. This solution was added dropwise to a vigorously stirred solution of potassium carbonate in water. The organic phase was separated, washed with water, dried, filtered and evaporated. The oily residue was converted into the nitrate salt in 2-propanol. 2,2'-Oxybispropane was added till turbid and the formed salt was allowed to crystallize. It was filtered off and dried, yielding 6 parts of 2-(2,4-dichlorophenyl)-2-[1-(1H-imidazol-1-yl)ethyl]-1,3-dithiolane; mp. 141.9° C. (compound 29).

B. PHARMACOLOGICAL EXAMPLES

EXAMPLE III

Activity against Erysiphe cichoracearum on gherkins upon foliar treatment

Young gherkin plants, about 10 days old, were sprayed with an aqueous solution containing 100, 10 or 1 ppm of the compound to be tested while controls were kept untreated. After drying of the plants, artificial infection with spores of *Erysiphe cichoracearum* was carried out by slightly rubbing the plants with a heavily infected leaf. At the 15th day after artificial infection the degree of fungal attack was evaluated by counting the number of spots per plant. The results given in column 1 of table II were the percentages of fungal attack in comparison with the untreated plants.

EXAMPLE IV

Activity against Erysiphe graminis on barley upon foliar treatment

Barley plants, about 8 cm in height, were sprayed with an aqueous solution containing 100, 10 or 1 ppm of the compound to be tested while controls were kept untreated. After 3-4 hours the plants were dusted with conidia of the fungus. The infected barley plants were then placed in a glass-house at about 22° C. and fungal attack was evaluated 10 days after the day of infection.

The results given in column 2 of table II were the percentages of fungal attack in comparison with the untreated plants.

EXAMPLE V

Activity against Uromyces appendiculatus on phaseolum beans upon foliar treatment Bean plants, having the primary leaves fully developed, were sprayed with an aqueous solution containing 250, 100 or 10 ppm of the compound to be tested while controls were kept untreated. After 3-4 hours the plants were infected with a suspension of spores of the fungus. After the plants were placed in an incubation room at 20° C. at 100% relative humidity for 24 hours they were placed in a glass-house at about 22° C. and fungal attack was evaluated 14 days after the day of infection.

The results given in column 3 of table II were the percentages of fungal attack in comparison with the untreated plants.

EXAMPLE VI

Activity against Botrytis cinerea on broad beans

Broad bean plants, about 10 cm in height, were sprayed with an aqueous solution containing 250, 100 or 10 ppm of the compound to be tested while controls were kept untreated. After 48 hours the plants were infected with a suspension of spores of the fungus. After incubating the infected plants for 2-3 days at 95-100% relative humidity and at 21° C. the fungal infection was evaluated.

The results given in column 4 of table II were the percentages of fungal attack in comparison with the untreated plants.

EXAMPLE VII

In-vitro antifungal screening

The subject compounds were tested against the following fungi:

| | |
|---|---|
| 1. *Coriolus versicolor* (white rot) | (C.v.) |
| 2. *Coniophora cerebella* (brown rot) | (C.c.) |
| 3. *Poria monticola* (brown rot) | (P.m.) |
| 4. *Chaetonium globosum* | (C.g.) |
| 5. *Pullularia pullulans* (blue stain) | (P.p.) |
| 6. *Aspergillus candidus* | (A.c.) |
| 7. *Penicillium islandicum* | (P.i.) |
| 8. *Cladosporium resinae* | (C.r.) |
| 9. *Aspergillus niger* | (A.n.) |
| 10. *Aspergillus flavus* | (A.f.) |
| 11. *Trichoderma viride* | (T.v.) |
| 12. *Mucor sp.* | (Muc.) |
| 13. *Rhizopus sp.* | (Rh.) |
| 14. *Absidia ramosa* | (A.r.) |

The fungi were grown on malt agar at 25° C. and 7 days old cultures were used in the tests.

10 mg of each test substance was dissolved first in 5 ml of ethanol/water 1/1 and the thus obtained stock solutions were diluted with water in such a way that the final concentration in the Petri-dish after mixing with the warm agar was 10, 1 or 0.1 ppm.

The agar was inoculated with ±1 mm$^3$ mycelium in the centre of the Petri-dish and incubated at 25° C. The results were evaluated after 14 days by measuring the diameter of fungal growth in mm. and expressed according to the following score system.

| score | growth in % of control |
|---|---|
| 0 | none |
| 1 | <25% |
| 2 | 25–50% |
| 3 | 50–75% |
| 4 | >75% |

The results were given in the following tables III-a and III-b.

TABLE III-a

Scores in in-vitro antifungal screening.

| com- | C.v. | | | C.c. | | | P.m. | | | C.g. | | | P.p. | | | A.c. | | | P.i. | | |
| pound | 10 | 1 | 0.1 | 10 | 1 | 0.1 | 10 | 1 | 0.1 | 10 | 1 | 0.1 | 10 | 1 | 0.1 | 10 | 1 | 0.1 | 10 | 1 | 0.1 |
|---|---|---|---|---|---|---|---|---|---|---|---|---|---|---|---|---|---|---|---|---|---|
| 1 | 0 | 0 | — | 2 | 4 | — | — | — | — | 0 | 0 | — | 1 | 1 | — | 0 | 3 | — | 0 | 4 | — |
| 7 | 0 | 1 | 4 | 0 | 3 | 4 | 0 | 0 | 4 | 0 | 0 | — | 0 | 2 | 4 | 0 | 0 | — | 0 | 3 | — |
| 8 | 0 | 0 | — | 0 | 0 | — | — | — | — | 0 | 0 | — | 1 | 1 | — | 0 | 0 | — | 0 | 2 | — |
| 9 | 0 | — | — | 0 | 3 | — | 0 | 0 | 1 | 0 | — | — | 1 | 1 | — | 0 | 0 | 0 | 0 | 2 | — |
| 29 | 0 | — | — | 0 | — | — | 0 | — | — | 0 | 2 | — | 1 | 3 | — | 0 | 0 | 2 | 1 | — | — |

TABLE II

| | Test | | | | | | | | | | | |
| | E. cichoracearum | | | E. graminis | | | U. appendiculatus | | | B. cinerea | | |
| Compound | 100 | 10 | 1 | 100 | 10 | 1 | 250 | 100 | 10 | 250 | 100 | 10 |
|---|---|---|---|---|---|---|---|---|---|---|---|---|
| 1 | 0 | 68 | 83 | 27 | 100 | 100 | 28 | 100 | 100 | 5 | 10 | 63 |
| 7 | 2 | 100 | 100 | 50 | 100 | 100 | 0 | 1 | 100 | 4 | 10 | 20 |
| 8 | 4 | — | — | — | — | — | 0 | 0 | 63 | 0 | 25 | 62 |
| 9 | 100 | 98 | 38 | 100 | 42 | 10 | 100 | 100 | 95 | 99 | 90 | 85 |
| 29 | 0 | 7 | 10 | 10 | 16 | 75 | 0 | 0 | 100 | 0 | 2 | 5 |

TABLE III-b

Scores in in-vitro antifungal screening.

| com- | C.r. | | | A.n. | | | A.f. | | | T.v. | | |
| pound | 10 | 1 | 0.1 | 10 | 1 | 0.1 | 10 | 1 | 0.1 | 10 | 1 | 0.1 |
|---|---|---|---|---|---|---|---|---|---|---|---|---|
| 1 | 0 | 0 | — | 0 | 3 | — | 1 | 3 | — | 3 | 4 | — |
| 7 | 0 | 0 | — | 0 | 0 | 4 | 0 | 2 | 4 | 1 | 4 | 4 |
| 8 | 0 | 0 | — | 0 | 0 | — | 0 | 1 | — | 1 | 4 | — |
| 9 | 0 | 1 | — | 0 | 0 | 3 | 0 | 1 | 2 | — | — | — |
| 29 | 1 | 1 | 3 | 0 | 0 | 3 | 0 | 2 | 3 | 3 | — | — |

C. FORMULATION EXAMPLES

EXAMPLE VIII

Dusts: The following substances were used to prepare (a) 5% and (b) a 2% dust:

(a)
5 parts of active substance
95 parts of talc;

(b)
2 parts of active substance
1 part of highly dispersed silicic acid
97 parts of talc.

The active substances were mixed with the carriers and ground and in this form can be processed to dusts for application.

EXAMPLE IX

Granulate: The following substances were used to prepare a 5% granulate:
5 parts of active substance
0.25 parts of epichlorohydrin
0.25 parts of cetyl polyglycol ether
3.25 parts of polyethylene glycol
91 parts of kaolin (particle size 0.3–0.8 mm.).

The active substance was mixed with epichlorohydrin and the mixture was dissolved in 6 parts of 2-propanone. Then polyethylene glycol and cetyl polyglycol ether were added. The resultant solution was sprayed on kaolin and the 2-propanone was evaporated in vacuo. Such a micro-granulate was advantageously used for combating soil fungi.

EXAMPLE XIII

Wettable powders: The following constituents were used to prepare (a) a 70%, (b) a 40%, (c) and (d) a 25% and (e) a 10% wettable powder:

(a)
70 parts of active substance
5 parts of sodium dibutylnaphthylsulfonate
3 parts of naphthalenesulfonic acid/phenolsulfonic acid/formaldehyde condensate (3:2:1).
10 parts of kaolin
12 parts of Champagne chalk.

(b)
40 parts of active substance
5 parts of sodium ligninsulfonate
1 part of sodium dibutylnaphthalenesulfonic acid
54 parts of silicic acid.

(c)
25 parts of active substance
4.5 parts of calcium ligninsulfonate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)
10 parts of active substance
3 parts of a mixture of the sodium salts of saturated fatty alcohol sulfates
5 parts of naphthalenesulfonic acid/formaldehyde condensate
82 parts of kaolin.

The active substances were intimately mixed in suitable mixers with the additives and ground in appropriate mills and rollers. Wettable powders of excellent wettability and suspension powder were obtained. These wettable powders can be diluted with water to give suspensions of the desired concentration and can be used in particular for leaf application.

EXAMPLE XIV

Emulsifiable concentrates: the following substances were used to prepare a 25% emulsifiable concentrate:
25 parts of active substance
2.5 parts of epoxidised vegetable oil
10 parts of an alkylarylsulfonate/fatty alcohol polyglycol ether mixture
5 parts of dimethyl formamide
57.5 parts of dimethylbenzene.

By diluting such a concentrate with water it was possible to prepare emulsions of the desired concentration, which were especially suitable for leaf application.

What is claimed is:

1. A compound selected from the group consisting of an imidazole derivative having the formula

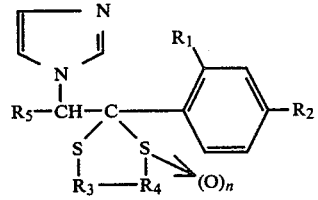

the possible stereochemically isomeric forms, the acid addition salts and the metal salt complexes thereof, wherein:

$R_1$ is hydrogen or halo;

$R_2$ is halo;

$R_3$ and $R_4$ together with the sulfur atoms to which they are attached and the bridging carbon atom form a 5- or 6-membered ring which is optionally substituted with a $C_1$–$C_3$-lower alkyl group;

$R_5$ is hydrogen or $C_1$–$C_4$-lower alkyl;

and n is 0, 1 or 2.

2. A compound according to claim 1 wherein $R_1$ is hydrogen or chloro and $R_2$ is chloro.

3. A compound according to claim 1 wherein $R_1$ is hydrogen or chloro, $R_2$ is chloro, and $R_5$ is hydrogen.

4. A compound according to claim 1 wherein $R_1$ and $R_2$ are both chloro, $R_3$ and $R_4$ together with the sulfur atoms to which they are attached and the bridging carbon atom form a 5-membered ring which is optionally substituted with a methyl, ethyl or propyl group and $R_5$ is hydrogen.

5. A compound selected from the group consisting of 1-[[2-(2,4-dichlorophenyl)-1,3-dithiolan-2-yl]methyl]-1H-imidazole, the possible stereochemically isomeric forms, the acid addition salts and the metal salt complexes thereof.

6. A compound selected from the group consisting of 1-[[2-(2,4-dichlorophenyl)-4-methyl-1,3-dithiolan-2-yl]methyl]-1H-imidazole, the possible stereochemically isomeric forms, the acid addition salts and the metal salt complexes thereof.

7. A compound selected from the group consisting of 1-[[2-(2,4-dichlorophenyl)-4-ethyl-1,3-dithiolan-2-yl]methyl]-1H-imidazole, the possible stereochemically isomeric forms, the acid addition salts and the metal salt complexes thereof.

8. A compound selected from the group consisting of 1-[[2-(2,4-dichlorophenyl)-4-propyl-1,3-dithiolan-2-yl]methyl]-1H-imidazole, the possible stereochemically isomeric forms, the acid addition salts and the metal salt complexes thereof.

9. A compound selected from the group consisting of 2-(2,4-dichlorophenyl)-2-[1-(1H-imidazol-1-yl)ethyl]-1,3-dithiolane, the possible stereochemically isomeric forms, the acid addition salts and the metal salt complexes thereof.

10. An antimicrobial composition comprising inert carrier materials and as an active ingredient an antimicrobially effective amount of a compound selected from the group consisting of an imidazole derivative having the formula

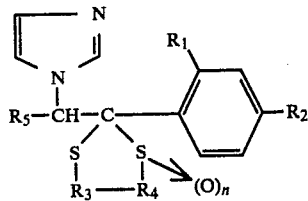

the possible stereochemically isomeric forms, the acid addition salts and the metal salt complexes thereof, wherein:
 $R_1$ is hydrogen or halo;
 $R_2$ is halo;
 $R_3$ and $R_4$ together with the sulfur atoms to which they are attached and the bridging carbon atom form a 5- or 6-membered ring which is optionally substituted with a $C_1$-$C_3$-lower alkyl group;
 $R_5$ is hydrogen or $C_1$-$C_4$-lower alkyl;
 and n is 0, 1 or 2.

11. An antimicrobial composition according to claim 10 wherein $R_1$ is hydrogen or chloro and $R_2$ is chloro.

12. An antimicrobial composition according to claim 10 wherein $R_1$ is hydrogen or chloro, $R_2$ is chloro, and $R_5$ is hydrogen.

13. An antimicrobial composition according to claim 10 wherein $R_1$ and $R_2$ are both chloro, $R_3$ and $R_4$ together with the sulfur atoms to which they are attached and the bridging carbon atom form a 5-membered ring which is optionally substituted with a methyl, ethyl or propyl group and $R_5$ is hydrogen.

14. An antimicrobial composition according to claim 10 wherein said active ingredient is a compound selected from the group consisting of 1-[[2-(2,4-dichlorophenyl)-1,3-dithiolan-2-yl]methyl]-1H-imidazole, the possible stereochemically isomeric forms, the acid addition salts and the metal salt complexes thereof.

15. An antimicrobial composition according to claim 10 wherein said active ingredient is a compound selected from the group consisting of 1-[[2-(2,4-dichlorophenyl)-4-methyl-1,3-dithiolan-2-yl]-methyl]-1H-imidazole, the possible stereochemically isomeric forms, the acid addition salts and the metal salt complexes thereof.

16. An antimicrobial composition according to claim 10 wherein said active ingredient is a compound selected from the group consisting of 1-[[2-(2,4-dichlorophenyl)-4-ethyl-1,3-dithiolan-2-yl]-methyl]-1H-imidazole, the possible stereochemically isomeric forms, the acid addition salts and the metal salt complexes thereof.

17. An antimicrobial composition according to claim 10 wherein said active ingredient is a compound selected from the group consisting of 1-[[2-(2,4-dichlorophenyl)-4-propyl-1,3-dithiolan-2-yl]-methyl]-1H-imidazole, the possible stereochemically isomeric forms, the acid addition salts and the metal salt complexes thereof.

18. An antimicrobial composition according to claim 10 wherein said active ingredient is a compound selected from the group consisting of 2-(2,4-dichlorophenyl)-2-[1-(1H-imidazol-1-yl)ethyl]-1,3-dithiolane, the possible stereochemically isomeric forms, the acid addition salts and the metal salt complexes thereof.

19. A method of protecting crops from microbial attack which comprises treating said crops with an effective antimicrobial amount of a compound selected from the group consisting of an imidazole derivative having the formula

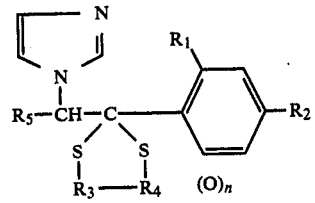

the possible stereochemically isomeric forms, the acid addition salts and the metal salt complexes thereof, wherein:
 $R_1$ is hydrogen or halo;
 $R_2$ is halo;
 $R_3$ and $R_4$ together with the sulfur atoms to which they are attached and the bridging carbon atom form a 5- or 6-membered ring which is optionally substituted with a $C_1$-$C_3$-lower alkyl group;
 $R_5$ is hydrogen or $C_1$-$C_4$-lower alkyl;
 and n is 0, 1 or 2.

20. A method according to claim 19 wherein $R_1$ is hydrogen or chloro and $R_2$ is chloro.

21. A method according to claim 19 wherein $R_1$ is hydrogen or chloro, $R_2$ is chloro, and $R_5$ is hydrogen.

22. A method according to claim 19 wherein $R_1$ and $R_2$ are both chloro, $R_3$ and $R_4$ together with the sulfur atoms to which they are attached and the bridging carbon atom form a 5-membered ring which is optionally substituted with a methyl, ethyl or propyl group and $R_5$ is hydrogen.

23. A method of protecting crops from microbial attack which comprises treating said crops with an effective antimicrobial amount of a compound selected from the group consisting of an imidazole derivative having the formula

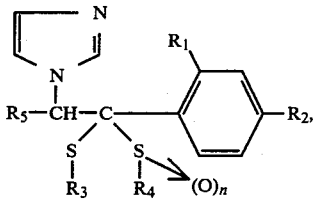

(I)

the possible stereochemically isomeric forms, the acid addition salts and the metal salt complexes thereof, wherein:

$R_1$ and $R_2$ are each independently selected from the group consisting of hydrogen, halo and methyl;

$R_3$ and $R_4$ are each independently selected from the group consisting of $C_1$–$C_6$-lower alkyl and $C_3$–$C_4$-lower alkenyl, or $R_3$ and $R_4$ form, together with the sulfur atoms to which they are attached and the bridging carbon atom, a 5-, 6- or 7-membered ring which is optionally substituted with 1 to 4 $C_1$–$C_4$-lower alkyl groups;

$R_5$ is a member selected from the group consisting of hydrogen; and n is 0, 1 or 2.

* * * * *